United States Patent [19]

Wiedmer

[11] Patent Number: 4,835,169
[45] Date of Patent: May 30, 1989

[54] FUNGICIDES

[75] Inventor: Hans Wiedmer, Therwil, Switzerland

[73] Assignee: Sandoz Ltd., Basel, Switzerland

[21] Appl. No.: 129,254

[22] Filed: Dec. 7, 1987

[30] Foreign Application Priority Data

Dec. 9, 1986 [GB] United Kingdom ............... 8629360

[51] Int. Cl.⁴ ............................................. A01N 43/64
[52] U.S. Cl. .................................................... 514/383
[58] Field of Search ............ 514/383, 388, 187, 255, 514/387

[56] References Cited

U.S. PATENT DOCUMENTS

| 4,305,953 | 12/1981 | Pfliegel et al. | 514/388 |
| 4,405,605 | 9/1983 | Itzel | 514/255 |
| 4,621,080 | 11/1986 | Dombay et al. | 514/187 |
| 4,664,696 | 5/1987 | Schaub | 514/383 |

FOREIGN PATENT DOCUMENTS

| 2059773 | 4/1981 | European Pat. Off. . |
| 0047594 | 3/1982 | European Pat. Off. . |
| 92961 | 2/1983 | European Pat. Off. . |

OTHER PUBLICATIONS

The Pesticide Manual, (8th Ed.), p. 128.

Primary Examiner—Douglas W. Robinson
Assistant Examiner—Raymond J. Henley, III
Attorney, Agent, or Firm—Gerald D. Sharkin; Richard E. Vila; Diane E. Furman

[57] ABSTRACT

The invention provides a method of combatting fungal diseases with the aid of
(a) the compound of formula I

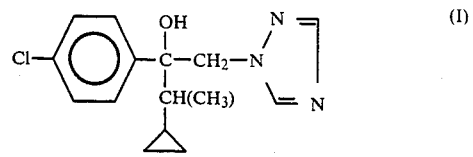

and
(b) carbendazim, and fungicidal compositions comprising said compounds.

8 Claims, No Drawings

FUNGICIDES

The present invention relates to fungicides.

The invention provides a method for combatting fungal diseases in plants with the aid of
(a) the compound of formula I

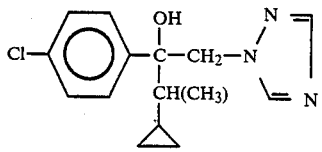

hereinafter referred to as "Compound A", and
(b) carbendazim.

Compound A is a known broad spectrum triazole fungicide (UKP No. 2136423B) showing high activity against most of the economically important fungi of the Ascomycetes and Basidiomycetes, and some of the Deuteromycetes.

Carbendazim is the common name for methylbenzimidazol-2-ylcarbamate, a known systemic fungicide controlling a wide range of pathogens in i.a. fruit, vegetables, cereals, ornamentals and grapes.

It has now been found that the use of carbendazim in combination with Compound A (Combination of the invention) is surprisingly effective in the combatting of fungi.

Thus more than an additive effect is observed against Helminthosporium on barley and Pseudocerosporella on wheat. The efficacy of the combination of the invention will depend on the particular fungi (disease) to be combatted, the crop involved, the weight ratio of Compound A:carbendazim, the mode of application, and other parameters. The combination of the invention is particularly appropriate for combatting fungi in cereals, vine, fruit trees, sugar beet and rape, for example against foot diseases in cereals, against powdery mildew, black rot and brenner in vine, against monilia in fruit trees, against cercospora, powdery mildew and ramularia in sugar beet and against alternaria, sclerotinia and cylindrosporium in rape.

Accordingly, the invention provides an improved method of combatting fungal diseases in plants, especially in cereals, vine, fruit trees, sugar beet and rape, which comprises applying to the plant locus, in admixture or separately, Compound A and carbendazim in an effective aggregate amount.

The combination may for example be applied in spray form, e.g. employing appropriate dilutions of a soluble concentrate or of a wettable formulation in water.

Suitable application rates for field crops such as cereals, sugar beet or rape are e.g. from 40 to 100 g, especially from 50 to 100 g, particularly from 60 to 80 g of Compound A per hectare and from 50 to 300 g, particularly from 80 to 250 g, more particularly from 100 to 150 g of carbendazim per hectare of crop locus. For crops such as fruit trees and grapes (grape vines), the application rate is usually expressed in terms of concentrations. Spray liquors suitable for use in grapes or orchards including fruit trees such as apple trees comprise e.g. from 0.5 to 2.0 g, particularly from 0.8 to 1.2 g per hectoliter of Compound A and from 2.0 to 50 g, more particularly from 2.5 to 25 g per hectoliter of carbendazim; the treatment involves usually foliar application till the run-off. In grape vines this corresponds in general with a spray-volume of about 800 to 1400 liter per hectare, depending i.a. on the growth stage of the crop.

The weight ratio will depend on various factors such as the mode of application and the crops involved. In general the weight ratio of Compound A:carbendazim lies in the range of 2:1 to 1:100. The optimal ratio Compound A:carbendazim will normally lie in the range of from 1:0.6 to 1:5, preferably of from 1:0.6 to 1:2.5. Examples of suitable weight ratios of Compound A:carbendazim for use in cereals are 1:0.6, 1:1.25, 1:1.66, 1:1.8 and 1:2.5.

The invention also provides fungicidal composition comprising Compound A and carbendazim, e.g. in a weight ratio within the range specified hereinabove.

Such compositions of the invention may be formulated in any conventional form, for example in the form of a twin packet, or of an emulsifiable concentrate, a soluble concentrate, a wettable powder or water dispersible granule. Such compositions may be produced in conventional manner, e.g. by mixing Compound A and carbendazim with appropriate adjuvants such as diluents and optionally other formulating ingredients such as surfactants.

The term diluent as used herein means any liquid or solid agriculturally acceptable material—including carriers—which may be added to the active constituents to bring them in a suitable application or commercial form. It can for example be talc, kaolin, diatomaceous earth, mineral oil, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty sulphate, an ethoxylated alkylphenol and an ethoxylated fatty alcohol.

In general, the formulations include from 0.01 to 90% by weight of active agent, from 0 to 20% agriculturally acceptable surfactant and 10 to 99.99% solid or liquid diluent, the active agent comsisting of Compound A and carbendazim and optionally other active agents. The formulations may additionally contain additives such as pigments, thickeners and the like.

The invention is illustrated by the following examples, wherein parts and percentages are by weight.

FORMULATION EXAMPLE 1

Wettable Powder

27% of Compound A
50% of carbendazim
1% of sodium dialkylnaphthalene sulphonate
6% of lignin sulphonate
6% silica
10% kaolin.

The above components are combined and milled until less than 5 micron in in particle size.

FORMULATION EXAMPLE 2

Soluble Concentrate

A mixture of
160 g of Compound A
300 g of carbendazim
100 g of anti-freezing agent (e.g. propylene glycol)
50 g of surfactant (e.g. a mixture of alkyl polyalkoxycarboxymethyl sodium salt)

3 g of thickener
10 g of antifoam
in 1 liter of water
is stirred in a vessel and then milled in a pearl mill until 1-2 micron in particle size.

GREENHOUSE TEST

In vivo employing Psdueocercosporella on wheat

Wheat is cultivated in a mixture of peat and sand in plastic pots of 6 cm diameter for 6 days. The plants are sprayed with aqueous spray liquors containing the Compound A, carbendazim or mixtures thereof (hereinafter a.i.) in various concentrations. The treatment comprises foliar spraying to near run off. After drying, the plants are inoculated by dusting them with freshly collected conidia and are then incubated during 4 weeks in an incubation chamber at 60-80% relative humidity, 16 hours daylight and 25°-30° C. The efficacy of the a.i. is determined by comparing the degree of fungal attack on the treated with that on untreated, similarly inoculated check plants, and is expressed in % control for a given test concentration. Each a.i. is tested in 5 concentrations (125, 31, 7.8, 2.0 and 5.0 ppm). This allows for the determination of the EC 90 exp. value, i.e. the concentration of each a.i. allowing 90% disease control. The experimental result (EC 90 exp.) for a given weight ratio of Compound A:carbendazim is compared with the corresponding EC 90 theor. value, i.e. the concentration of that particular mixture allowing 90% disease control calculated according to Wadley.

$$EC(A + C)90 \text{ theor} = \frac{a + b}{\frac{a}{EC(A)90 \text{ exp.}} + \frac{b}{EC(C)90 \text{ exp.}}}$$

wherein a and b are the ratios of Compound A and carbendazim in the mixture resp. and the indexes (A), (C) and (A+C) refer to the EC 90 values of the Compound A, carbendazim and the a:b mixture of Compound A and carbendazim resp. In the case of synergism EC (A+C)90 theor. is greater than EC(A+C)90 exp., or $$SF = \frac{EC(A + C)90 \text{ theor}}{EC(A + C)90 \text{ exp}} > 1$$

Analogous tests are run with Helminthosporium on barley (incubation 6 days instead of 4 weeks).

The results in which EC 90 values are expressed in ppm or mg/liter are as follows:

| | EC90 exp. | EC90 theor. | SF |
|---|---|---|---|
| 1. Pseupocercosporella/wheat | | | |
| Compound A | 38.0 | | |
| Carbendazim | 117.0 | | |
| Weight ratio of Compound A:carbendazim | | | |
| 1.0:0.6 | 30.0 | 50.88 | 1.7 |
| 1.0:1.25 | 35.0 | 60.81 | 1.7 |
| 1.0:2.50 | 45.0 | 73.40 | 1.6 |
| 2. Helminthosporium/barley | | | |
| Compound A | 10.0 | | |

| | EC90 exp. | EC90 theor. | SF |
|---|---|---|---|
| Carbendazim | 1000.0 | | |
| Weight ratio of Compound A:carbendazim | | | |
| 1.0:0.6 | 11.0 | 15.9 | 1.4 |
| 1.0:1.25 | 9.0 | 22.22 | 2.5 |
| 1.0:2.5 | 26.0 | 34.15 | 1.3 |

I claim:
1. A fungicide composition comprising a solid or liquid agriculturally acceptable diluent and a fungicidally effective amount of the combination of
    (a) the compound of the formula I

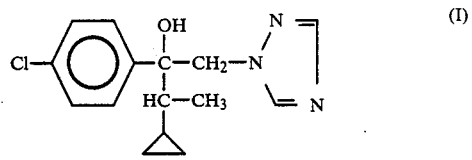

and
    (b) carbendazim, the weight ratio of the compound of the formula I to carbendazim being in the range of from 1:0.6 to 1:2.5.
2. The method of combatting fungal diseases in plants, which comprises applying to the plant locus a fungicidally effective aggregate amount of
    (a) the compound of the formula I

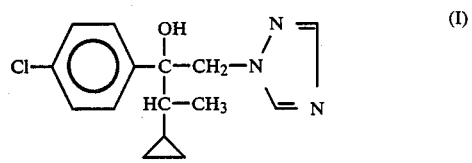

and
    (b) carbendazim, the weight ratio of the compound of the formula I to carbendazim being in the range of from 1:0.6 to 1:2.5.
3. The method of claim 2, wherein the plants are field crops, and employing from 40 to 100 g of the compound of formula I and from 50 to 300 g of carbendazim per hectare of crop locus.
4. The method of claim 3, employing from 50 to 100 g of the compound of formula I and from 80 to 250 g of carbendazim per hectare of crop locus.
5. The method of claim 2, wherein the plants are grape vines or orchards, employing a spray liquid comprising from 0.5 to 2.0 g per hectoliter of the compound of formula I and from 2.0 to 50 g per hectoliter of carbendazim.
6. The method of claim 5, employing a spray liquid comprising from 0.8 to 1.2 g per hectoliter of the compound of formula I and from 2.5 to 25 g per hectoliter of carbendazim.
7. The method of claim 2 in which the plant is a cereal, vine, fruit tree, sugar beet or rape plant.
8. The method of claim 7 in which the fungal disease is Helminthosporium in barley or Pseudocerosporella in wheat.

* * * * *